United States Patent [19]

Bosies et al.

[11] Patent Number: 4,492,659
[45] Date of Patent: Jan. 8, 1985

[54] PHOSPHOLIPID COMPOUND

[75] Inventors: Elmar Bosies, Weinheim; Rudi Gall, Hirschberg; Günter Weimann, Weinheim-Lützelsachsen; Uwe Bicker, Lorsch; Wulf Pahlke, Mannheim, all of Fed. Rep. of Germany

[73] Assignee: Boehringer Mannheim GmbH, Mannheim, Fed. Rep. of Germany

[21] Appl. No.: 395,954

[22] Filed: Jul. 7, 1982

[30] Foreign Application Priority Data

Jul. 11, 1981 [DE] Fed. Rep. of Germany ...... 3127503

[51] Int. Cl.³ .............................................. C07F 9/02
[52] U.S. Cl. ............................... 260/925; 260/945; 424/199
[58] Field of Search ............... 260/925, 945; 424/199

[56] References Cited

U.S. PATENT DOCUMENTS

| 4,119,714 | 10/1978 | Kay et al. ............... | 424/199 |
| 4,159,988 | 7/1979 | Eibl et al. ............... | 260/925 |
| 4,372,949 | 2/1983 | Kodama et al. .......... | 424/199 |

FOREIGN PATENT DOCUMENTS

| 40039 | 11/1981 | European Pat. Off. ...... | 424/199 |
| 2009341 | 9/1971 | Fed. Rep. of Germany ...... | 424/199 |
| 138216 | 10/1979 | German Democratic Rep. ...... | 260/925 |
| 5002636 | 1/1980 | Japan ...................... | 424/199 |

*Primary Examiner*—Anton H. Sutto
*Attorney, Agent, or Firm*—Felfe & Lynch

[57] ABSTRACT

The present invention provides phospholipids of the general formula:

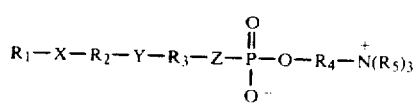

wherein X is a valency bond, an oxygen or sulphur atom or a sulfonyl, sulfinyl, phenylene, cycloaklylene, carbonylamino, aminocarbonyl, ureido or carbonyl group, $R_1$ is a hydrogen atom or a straight-chained or branched, saturated or unsaturated aliphatic hydrocarbon radical containing up to 18 carbon atoms, which is optionally substituted one or more times by halogen, alkoxy, alkylthio, alkanesulfinyl, alkanesulfonyl, carbalkoxy or phenyl, $R_2$ is a straight-chained or branched, saturated or unsaturated divalent aliphatic hydrocarbon radical containing up to 18 carbon atoms, which is optionally substituted one or more times by halogen, alkoxy, alkylthio, alkanesulphinyl, alkanesulphonyl, carbalkoxy or phenyl, Y is an oxygen atom or a —O—CO—O—, —O—CO—NH— or —O—CS—NH— group, $R_3$ is a straight-chained or branched, saturated or unsaturated divalent aliphatic hydrocarbon radical containing 2 to 8 carbon atoms, which can also be part of a cycloalkane ring system and is optionally substituted one or more times by hydroxyl, halogen, alkylthio, alkanesulphinyl, alkanesulfonyl, nitrile, alkoxycarbonyl, carboxamido optionally substituted by alkyl radicals, cycoalkyl, optionally substituted phenyl or alkoxy, which in turn is optionally substituted by phenyl, hydroxyl, alkoxy, alkylthio, alkanesulfinyl, alkanesulfonyl, optionally acylated amino, alkoxycarbonyl, nitrile or carboxamido optionally substituted by alkyl radicals, Z is an oxygen or sulfur atom, $R_4$ is a straight-chained or branched alkylene radical containing 2 to 5 carbon atoms and $R_5$ is a hydrogen atom or a lower alkyl radical, with the proviso that when X is a valency bond, $R_1$ and $R_2$ together represent an unsubstituted, straight-chained or branched, saturated or unsaturated divalent aliphatic hydrocarbon chain containing up to 18 carbon atoms, Y, $R_4$ and $R_5$ have the above-given meanings and Z is an oxygen atom, $R_3$ cannot be a propylene or 2-methylpropylene chain optionally substituted by hydroxyl, alkoxy or benzyloxy and with the proviso that when X is a valency bond, $R_1$ and $R_2$ together signify an alkyl radical containing up to 18 carbon atoms and substituted by halogen or phenyl, Y and Z are oxygen atoms and $R_4$ and $R_5$ have the above-given meanings, $R_3$ cannot be a propylene or 2-hydroxypropylene chain; and the pharmacologically acceptable salts thereof.

The invention also provides pharmaceutical compositions containing such compounds, having cancerostatic action without inducing thrombocyte aggregation.

6 Claims, No Drawings

PHOSPHOLIPID COMPOUND

This invention relates to new phospholipid compounds and with pharmaceutical compositions containing them. In additional aspect the invention relates to processes for making such phospholipid compounds.

Federal Republic of Germany Patent Specification No. 20 09 341 describes 3-octadecyloxypropan-1-ol-phosphoric acid monocholine ester as an immunological adjuvant. Federal Republic of Germany Patent Specification No. 20 09 342 describes the 3-hydroxy derivative thereof as an agent for increasing the natural resistance of an organism and Federal Republic of Germany Patent Specification No. 26 19 686 describes the 2-methoxy derivative thereof as an antitumour agent. Finally, Federal Republic of Germany Patent Specification No. 26 19 715 describes dodecyloxypropylphosphorylcholine as being a "tumour antigen".

Japanese Patent Specification No. J5 5002-636 describes in general terms some glycerophosphorylcholines with urethane and thiourethane groupings. Federal Republic of Germany Patent Specification No. 27 17 597 describes phospholipids, the alkyl chain of which can be substituted in the 3-position of the glycerol by halogen or phenyl.

We have now found that the new phospholipids of the present invention have an outstanding cancerostatic action but, contrary to the above-mentioned phospholipids, do not induce a thrombocyte aggregation.

Thus, according to the present invention, there are provided new compounds of the general formula:

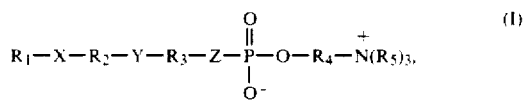

wherein X is a valency bond, an oxygen or sulphur atom or a sulfonyl, sulfinyl, phenylene, cycloalkylene, carbonylamino, aminocarbonyl, ureido or carbonyl group, $R_1$ is a hydrogen atom or a straight-chained or branched, saturated or unsaturated aliphatic hydrocarbon radical containing up to 18 carbon atoms which is optionally substituted one or more times by halogen, alkoxy, alkylthio, alkanesulfinyl, alkanesulfonyl, carbalkoxy or phenyl, $R_2$ is a straight-chained or branched, saturated or unsaturated divalent aliphatic hydrocarbon radical containing up to 18 carbon atoms, which is optionally substituted one or more times by halogen, alkoxy, alkylthio, alkanesulfinyl, alkanesulfonyl, carbalkoxy or phenyl, Y is an oxygen atom or a —O—CO—O—, —O—CO—NH— or —O—CS—NH— group, $R_3$ is a straight-chained or branched, saturated or unsaturated divalent aliphatic hydrocarbon radical containing 2 to 8 carbon atoms, which can also be part of a cycloalkane ring system and is optionally substituted one or more times by hydroxyl, halogen, alkylthio, alkanesulfinyl, alkanesulfonyl, nitrile, alkoxycarbonyl, carboxamido optionally substituted by alkyl radicals, cycloalkyl, optionally substituted phenyl or alkoxy, which in turn is optionally substituted by phenyl, hydroxyl, alkoxy, alkylthio, alkanesulfinyl, alkanesulfonyl, optionally acylated amino, alkoxycarbonyl, nitrile or carboxamido optionally substituted by alkyl radicals, Z is an oxygen or sulphur atom, $R_4$ is a straight-chained or branched divalent alkylene radical containing 2 to 5 carbon atoms and $R_5$ is a hydrogen atom or a lower alkyl radical, with the proviso that when X is a valency bond, $R_1$ and $R_2$ together represent an unsubstituted, straight-chained or branched, saturated or unsaturated divalent aliphatic chain containing up to 18 carbon atoms, Y, $R_4$ and $R_5$ have the above-given meanings and Z is an oxygen atom, $R_3$ cannot be a propylene or 2-methylpropylene chain optionally substituted by hydroxyl, alkoxy or benzyloxy and with the proviso that when X is a valency bond, $R_1$ and $R_2$ together signify an alkyl radical containing up to 18 carbon atoms and substituted by halogen or phenyl, Y and Z are oxygen atoms and $R_4$ and $R_5$ have the above-given meanings, $R_3$ cannot be a propylene or 2-hydroxypropylene chain; and the pharmacologically acceptable salts thereof.

When $R_5$ is an alkyl radical, it contains up to 6 carbon atoms and is preferably a methyl or ethyl radical.

In all cases, alkoxy, alkoxycarbonyl, alkylthio, alkanesulfinyl, and alkanesulfonyl, mean, as a rule, radicals containing up to 6 carbon atoms but can also be radicals containing up to 20 carbon atoms, for example octadecyloxy, tetradecyloxy, octyloxy and the like.

An acylamino radical is preferably an amino group substituted by acetyl or methanesulphonyl.

The cycloalkylene radical X is to be understood to be a radical containing 3 to 8 carbon atoms and especially a cyclopropyl, cyclopentyl and cyclohexyl radical.

Cycloalkane rings which can be components of the alkylene chain of $R_3$ or which can be present as substituents of $R_3$ are preferably cyclopentane, cyclohexane or cycloheptane rings.

Halogen means fluorine, chlorine, bromine and iodine, fluorine and chlorine being preferred.

The grouping $R_1$—X—$R_2$ means, when X is a valency bond, an aliphatic hydrocarbon radical containing up to 20 carbon atoms, which can be straight-chained or branched and saturated or unsaturated. The unsaturated radical can contain up to 4 double bonds but preferably contains 1 or 2 double bonds.

The group $R_4$ is preferably the —$CH_2$—$CH_2$— radical.

The phenyl radical referred to in the definition of $R_3$ can be substituted one or more times by alkyl, alkoxy or halogen.

The present invention also provides a process for the preparation of compounds of general formula (I), wherein a compound of the general formula:

in which $R_1$, $R_2$, $R_3$, X, Y and Z have the same meanings as above is either (a) reacted with a compound of the general formula:

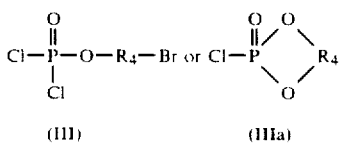

in which $R_4$ has the same meaning as above, in the presence of an acid-binding agent, the reaction product, when using a compound of general formula (III), then selectively hydrolysed and the remaining bromine atom replaced by an optionally alkylated ammonium group or, when using a compound of general formula (IIIa), treated directly with optionally alkylated ammonia; or (b) converted into a compound of the general formula:

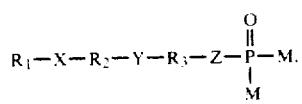

in which $R_1$, $R_2$, $R_3$, X, Y and Z have the meanings given above and M is hydroxyl, chlorine, bromine or alkylthio, and this reacted with a compound of the general formula:

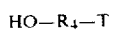

in which $R_4$ has the above-given meaning and T is chlorine or bromine or the grouping $N(R_5)_3{}^+ Hal^-$, wherein $R_5$ has the above-given meaning and Hal is chloride, bromide or iodide, with the proviso that when T is chlorine or bromine, the intermediate thus obtained is subsequently quaternised with an amine of the general formula $N(R_5)_3$, in which $R_5$ has the above-given meaning; or (c) reacted with a compound of the general formula:

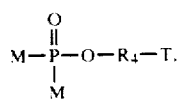

in which M, $R_4$ and T have the above-given meanings, in the presence of an acid- and water-binding agent; and the compound obtained is, if desired, converted into an internal salt and/or oxidised and/or converted into a pharmacologically acceptable salt.

All the above-described processes are carried out in known manner.

As a rule, process (a) is carried out in such a manner that an alcohol or thiol of general formula (II) is reacted with a bromoalkylphosphoric acid monoester dichloride of general formula (III) in the presence of an acid-binding agent, for example triethylamine, in an anhydrous, inert organic solvent, for example a chlorinated hydrocarbon or toluene, at a temperature of from about the freezing point to ambient temperature. The selective hydrolysis of the phosphoric acid diester monochloride obtained is achieved directly in a two-phase mixture by the addition of an aqueous solution of potassium chloride at a temperature of from 0° to 50° C. For the substitution of the remaining bromine atom by an optionally alkylated ammonium group, ammonia or an alkylamine is dissolved in a medium which sufficiently well dissolves not only the phosphoric acid diester but also ammonia or the amine, for which purpose mixtures of acetonitrile or lower alcohols with chlorinated hydrocarbons are especially preferred, the reaction being completed at a temperature of from 20° to 70° C.

It is also possible to proceed stepwise by first introducing an alkylammonium radical and subsequently reacting with alkyl halide to give a di- or trialkylammoniumalkyl ester.

If an alcohol or thiol of general formula (II) is reacted with a phosphoric acid ester chloride of general formula (IIIa), this takes place under the same reaction conditions as previously described. The reaction with optionally alkylated ammonia is preferably carried out in acetonitrile as solvent at 50° to 100° C. in a pressure vessel.

The removal of residual halide ions is preferably carried out in a lower alcohol by means of silver acetate or silver oxide.

All intermediates, as well as end products, can be purified by column chromatography with conventional elution agents, for example diethyl ether, ligroin, chlorinated hydrocarbons, lower alcohols or mixtures thereof, on silica gel. In the case of betaine-like end products, it is preferable to add some water to the elution agent used.

In the case of process (b), when M signifies chlorine or bromine, the reaction of a compound of general formula (II) with a phosphorus oxyhalide to give a phosphoric acid ester dihalide of general formula (IV) is carried out in an inert, anhydrous solvent, for example, a halogenated hydrocarbon, in the presence of an acid acceptor, preferably pyridine or quinoline. The reaction temperature is from 0° to 40° C. The product can be isolated or, without isolation, reacted with an alcohol of general formula (V), with the addition of further pyridine or quinoline, at a temperature of from 0° to 40° C. As solvents for this purpose, it is preferred to use halogenated hydrocarbons, as well as acetonitrile or trichloroacetonitrile.

When M signifies hydroxyl, the compound of general formula (IV) can be prepared by generally used processes, for example by hydrolysis of the corresponding phosphoric acid ester dihalide or by hydrogenolysis of the corresponding phosphoric acid ester diphenyl ester. The further reaction with alcohols of general formula (V) is carried out in the presence of sulphonic acid halides, for example p-toluenesulphochloride or triisopropylbenzenesulfochloride. As solvent, use is made of dimethylformamide with an addition of pyridine or of pyridine alone. As a rule, the reaction temperature is from 0° to 40° C. As activating and water-removing agent, dicyclohexylcarbodiimide can also be very well used.

When M is an alkylthio radical, the compound of general formula (IV) can be obtained by reacting a compound of general formula (II) with a dialkali metal salt of a thiophosphoric acid alkyl ester. The agent splitting off water is preferably dicyclohexylcarbodiimide in pyridine. The reaction is carried out at ambient temperature. The so-obtained alkylthiophosphoric acid ester is reacted with an alcohol of general formula (V) in the presence of iodine.

In all cases in which T in a compound of general formula (V) signifies chlorine or bromine, the intermediate so obtained is reacted under the conditions described for process (a) to give the desired end product.

The compounds of general formula (VI) in the case of process (c) can, when M is hydroxyl, be reacted with the generally used halogenation agents, for example phosphorus pentachloride, in the presence of an acid acceptor, for example pyridine, to give compounds of general formula (VI), in which M is chlorine or bromine, which can then be isolated or, without isolation, reacted with compounds of general formula (II). As acid acceptors, as a rule there are here also used nitrogen-containing bases, for example pyridine, quinoline or triethylamine. The preferred solvents are anhydrous halogenated hydrocarbons, as well as toluene. When M is hydroxyl or alkylthio, the reactions are carried out under the conditions described for process (b).

The alcohols and thiols of general formula (II) used as starting materials are also new. The alcohols of general formula (II) can be prepared, for example, by reducing the corresponding carboxylic acid esters with complex hydrides, for example lithium aluminium hydride. However, a diol of the general formula:

HO—R₃—OH (VII)

in which R₃ has the above-given meaning, can also be reacted with an equimolar amount of an appropriate halide, sulfonate, chloroformic acid ester, isocyanate or isothiocyanate to give the desired alcohol of general formula (II).

Thiols of general formula (II) can be synthesized from the alcohols of general formula (II) by known methods; for example, from an alcohol of general formula (II), there is prepared a halide or sulfonate, which is reacted with thiourea and the resulting isothiuronium salt is split with an alkali, the desired thiol of general formula (II) then being obtained by acidification.

The present invention also provides all stereoisomers of the compounds of general formula (I) which are obtained, for example, due to asymmetric carbon atoms or sulfoxide group or due to cis-trans isomerism. A separation of the products obtained in the form of a mixture can be carried out by means of known processes.

The pharmacologically acceptable salts are obtained in the usual manner, for example by neutralisation of the compounds of general formula (I) with non-toxic inorganic or organic acids, for example hydrochloric acid, sulfuric acid, phosphoric acid, hydrobromic acid, acetic acid, lactic acid, citric acid, malic acid, salicylic acid, malonic acid, maleic acid or succinic acid.

The new compounds of general formula (I) according to the present invention and the salts thereof can be administered enterally and parenterally in liquid or solid form. All conventional forms of administration can hereby be used, for example tablets, capsules, dragees, syrups, solutions, suspensions and the like. As injection medium, it is preferred to use water which contains the additives usual in the case of injection solutions, such as stabilizing agents, solubilizing agents and buffers.

Additives of this kind include, for example, tartrate and citrate buffers, ethanol, complex formers (such as ethylenediamine-tetraacetic acid in the non-toxic salts thereof) and high molecular weight polymers (such as liquid polyethylene oxide) for viscosity regulation. Liquid carrier materials for injection solutions must be sterile and are preferably placed into ampoules. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, also contain flavouring and/or sweetening agents.

The dosage used can depend upon various factors, such as the mode of administration, species, age and/or individual states. The doses to be administered daily are from about 0.05 to 100 mg./kg. of body weight.

Preferred compounds according to the present invention include, apart from those mentioned in the following Examples and the compounds derivable by the combination of all meanings of the substituents mentioned in the claims, also the following esters, which can be prepared by the processes described and claimed herein:

PREFERRED COMPOUNDS

1. [1-(11-caproylamidoundecyloxy)-3-propyl]-(2-trimethylammoniumethyl) phosphate
2. [1-(11-N-methylcaproylamidoundecyloxy)-3-propyl]-(2-trimethylammonium-ethyl) phosphate
3. [1-(11-pentanesulfonamidoundecyloxy)-3-propyl]-(2-trimethylammonium-ethyl) phosphate
4. [1-(11-N-methylpentanesulfonamidoundecyloxy)-3-propyl]-(2-trimethylammonium-ethyl) phosphate
5. [1-(11-N-n-butylacetamidoundecyloxy)-3-propyl]-(2-trimethylammonium-ethyl) phosphate
6. [1-(11-N-n-butylcarboxamidoundecyloxy)-3-propyl]-(2-trimethylammonium-ethyl) phosphate
7. [1-(11-N-n-butylthiocarboxamidoundecyloxy)-3-propyl]-(2-trimethylammonium-ethyl) phosphate
8. [1-(11-butoxycarbonylundecyloxy)-3-propyl]-(2-trimethylammonium-ethyl) phosphate
9. [1-(3-tetradecyloxypropoxy)-3-propyl]-2-trimethylammonium-ethyl) phosphate
10. [2-n-butyl-1-(11-N-n-butylcarboxamidoundecyloxy)-3-propyl]-(2-trimethylammonium-ethyl) phosphate
11. [2-n-butyl-1-(11-N-n-butyl-N-methylcarboxamidoundecyloxy)-3-propyl]-(2-trimethylammonium-ethyl) phosphate
12. [2-(2-methoxyethoxy)-methyl-1-octadecyloxy-3-propyl]-(2-trimethylammonium-ethyl) phosphate
13. (1-heptadecyloxy-2-methanesulfinylmethyl-3-propyl)-(2-trimethylammonium-ethyl) phosphate
14. [2-(2-aminoethyl)-1-hexadecyloxy-3-propyl]-(2-trimethylammonium-ethyl) phosphate
15. [2-(2-acetamidoethyl)-1-hexadecyloxy-3-propyl]-(2-trimethylammonium-ethyl) phosphate
16. [1-hexadecyloxy-2-(2-methanesulfonamidoethyl)-3-propyl]-(2-trimethylammonium-ethyl) phosphate
17. (2-cyanomethyl-1-octadecyloxy-3-propyl)-(2-trimethylammonium-ethyl) phosphate
18. (2-ethoxycarbonylmethyl-1-octadecyloxy-3-propyl)-(2-trimethylammonium-ethyl) phosphate
19. (2-carbamoylmethyl-1-octadecyloxy-3-propyl)-(2-trimethylammonium-ethyl) phosphate
20. [2-cyclopentyl-1-(6-undecyloxyhexyloxy)-3-propyl]-(2-trimethylammonium-ethyl) phosphate
21. [2-cyclohexylmethyl-1-(8-nonyloxyoctyloxy)-3-propyl]-(2-trimethylammonium-ethyl) phosphate
22. [1-(7-decyloxyheptyloxy)-2-(4-methylbenzyl)-3-propyl]-(2-trimethylammonium-ethyl) phosphate
23. [2-(5-chloro-2-methoxybenzyl)-1-(4-tridecyloxybutoxy)-3-propyl]-(2-trimethylammonium-ethyl) phosphate
24. (1-octadecyloxy-2-phenyl-3-propyl)-(2-trimethylammonium-ethyl) phosphate
25. (2-cyano-1-heptadecyloxy-3-propyl)-(2-trimethylammonium-ethyl) phosphate
26. (2-carbamoyl-1-heptadecyloxy-3-propyl)-(2-trimethylammonium-ethyl) phosphate
27. {2-hydroxy-1-[5-(3-octyloxypropoxy)-pentyloxy]-3-propyl}-(2-trimethylammonium-ethyl) phosphate
28. {2-methoxy-1-[7-(4-octylcyclohexyl)-heptyloxy]-3-propyl}-(2-trimethylammonium-ethyl) phosphate
29. [2-isopropoxy-1-(8-nonyloxyoctyloxy)-3-propyl]-(2-trimethylammonium-ethyl) phosphate
30. [1-octadecyloxy-2-(2-phenylethoxy)-3-propyl]-(2-trimethylammonium-ethyl) phosphate
31. [2-(2-hydroxyethoxy)-1-octadecyloxy-3-propyl]-(2-trimethylammonium-ethyl) phosphate 32. [1-heptadecyloxy-2-(2-methylthioethoxy)-3-propyl]-(2-trimethylammonium-ethyl) phosphate
33. [1-heptadecyloxy-2-(2-methanesulfinylethoxy)-3-propyl]-(2-trimethylammonium-ethyl) phosphate
34. [1-heptadecyloxy-2-(2-methanesulfonylethoxy]-3-propyl]-(2-trimethylammonium-ethyl) phosphate
35. [2-(2-aminoethoxy)-1-hexadecyloxy-3-propyl]-(2-trimethylammonium-ethyl) phosphate
36. [2-(2-acetamidoethoxy)-1-hexadecyloxy-3-propyl]-(2-trimethylammonium-ethyl) phosphate
37. [1-hexadecyloxy-2-(2-methanesulfonamidoethoxy)-3-propyl]-(2-trimethylammonium-ethyl) phosphate
38. (2-ethoxycarbonylmethoxy-1-heptadecyloxy-3-propyl)-(2-trimethylammonium-ethyl) phosphate
39. (2-cyanomethoxy-1-heptadecyloxy-3-propyl)-(2-trimethylammonium-ethyl) phosphate
40. (2-N-dodecylcarboxamidomethoxy-1-heptadecyloxy-3-propyl)-(2-trimethylammonium-ethyl) phosphate
41. (1-hexadecyloxy-2-methylthio-3-propyl)-(2-trimethylammonium-ethyl) phosphate
42. (1-hexadecyloxy-2-methanesulfinyl-3-propyl)-(2-trimethylammonium-ethyl) phosphate
43. (1-hexadecyloxy-2-methanesulfonyl-3-propyl)-(2-trimethylammonium-ethyl) phosphate
44. (2-amino-1-hexadecyloxy-3-propyl)-(2-trimethylammonium-ethyl) phosphate
45. [2,2-dimethyl-1-(6-undecyloxyhexyloxy)-3-propyl]-(2-trimethylammonium-ethyl) phosphate
46. {2-benzyl-2-methyl-1-[2-(10-n-butoxydecyloxy)ethoxy]-3-propyl}-(2-trimethylammonium-ethyl)-phosphate
47. (2-ethoxycarbonyl-2-methyl-1-octadecyloxy-3-propyl)-(2-trimethylammonium-ethyl) phosphate
48. [2-(2-pentadecanesulfinylethoxy)-4-pentyl]-(2-trimethylammonium-ethyl) phosphate
49. [2-(2-pentadecanesulfonylethoxy)-4-pentyl]-(2-trimethylammonium-ethyl) phosphate
50. [1-(4-tridecyloxybutoxy)-3-cyclopentyl]-(2-trimethylammonium-ethyl) phosphate
51. (1-hexadecylaminothiocarbonyloxy-2-methyl-3-propyl)-(2-trimethylammonium-ethyl) phosphate
52. S-(1-hexadecyloxy-2-methoxymethyl-3-propyl)-(2-trimethylammonium-ethyl) thiophosphate
53. S-(1-hetpadecyloxy-2-methyithiomethyl-3-propyl)-(2-trimethylammonium-ethyl) thiophosphate
54. S-(1-heptadecyloxy-2-isopropoxy-3-propyl)-(2-trimethylammonium-ethyl) thiophosphate
55. S-(1-hexadecyloxy-2-methylthio-3-propyl)-(2-trimethylammonium-ethyl) thiophosphate
56. S-(2,2-dimethyl-1-hexadecyloxy-3-propyl)-(2-trimethylammonium-ethyl) thiophosphate
57. S-(2-ethoxycarbonyl-2-methyl-1-octadecyloxy-3-propyl)-(2-trimethylammonium-ethyl) thiophosphate
58. S-(2-hexadecyloxy-4-pentyl)-(2-trimethylammonium-ethyl) thiophosphate
59. S-(1-octadecyloxy-3-cyclopentyl)-(2-trimethylammonium-ethyl) thiophosphate.

EXAMPLE 1

(2-Methoxymethyl)-1-octadecyloxy-3-propyl)-(2-trimethylammonium-ethyl) phosphate A solution of 1.1 g. (11 mMole) triethylamine and 1.1 g. (4.5 mMole) 2-bromoethylphosphoric acid ester dichloride in 15 ml. anhydrous toluene is added at 0° C. to 1.2 g. (3.2 mMole) 2-methoxymethyl-3-octadecyloxy-1-propanol in 15 ml. anhydrous toluene. The reaction mixture is stirred for 5 hours at 0° C. and overnight at ambient temperature. The reaction mixture is then mixed at 0° C. with 13 ml. 0.1N potassium chloride solution and vigorously stirred for 1 hour at 0° C. and for 2 hours at ambient temperature, whereafter the phases are separated and the organic phase is dried with anhydrous sodium sulphate and evaporated. 1.9 g. of a yellow oil remain behind which is dissolved in 40 ml. anhydrous methanol and 40 ml. anhydrous chloroform. Dry trimethylamine is passed in up to saturation point and the solution is then heated under reflux for 24 hours and evaporated on a rotary evaporator. The residue is dissolved in 70 ml. anhydrous methanol, mixed with 1 g. silver acetate and stirred for 4 hours at ambient temperature. The reaction mixture is filtered with suction, the residue is washed with anhydrous methanol and the filtrate is evaporated. A black oil remains behind which is purified for 12 hours over 100 g. silica gel (elution agent: methylene chloride/methanol/water in the ratio 65/25/4 v/v/v). The fractions containing the desired product are combined and evaporated, dried over phosphorus pentoxide and reprecipitated from chloroform/acetone. There is obtained 0.3 g. (17% of theory) of a hygroscopic substance; m.p. 70° C. (sinters), 248° to 250° C. (decomp.). The compound contains 2 moles of water of crystallization.

The 2-methoxymethyl-3-octadecyloxy-1-propanol used as starting material (wax-like substance; m.p. ≈30° C.) is obtained by reacting the monosodium salt of 2-methoxymethyl-1,3-propanediol with octadecyl bromide and subsequent column chromatographic separation.

In an analogous manner, there are obtained by using:

(a) 2-ethyl-3-octadecyloxy-1-propanol (wax-like substance) as starting material:
(2-ethyl-1-octadecyloxy-3-propyl)-(2-trimethylammonium-ethyl) phosphate containing 2 moles of water of crystallisation in a yield of 19% of theory; m.p. 80° C. (sinters), 264°–265° C. (decomp.)

(b) 2-methoxy-3-(2-methoxyoctadecyloxy)-1-propanol (wax-like substance; m.p. ≈25° C.) as starting material: [2-methoxy-1-(2-methoxyoctadecyloxy)-3-propyl]-(2-trimethylammonium-ethyl) phosphate containing 2.5 moles of water of crystallization in a yield of 22% of theory; m.p. 60° C. (sinters), 238°–240° C. (decomp.);

(c) 2-methoxy-3-[7-(4-octylphenyl)-heptyloxy]-1-propanol (wax-like substance) as starting material:
{2-methoxy-1-[7-(4-octylphenyl)-heptyloxy]-3-propyl}-(2-trimethylammonium-ethyl) phosphate containing 2 moles of water of crystallization in a yield of 24% of theory; m.p. 50° C. (sinters), 240°–243° C. (decomp.).

The 2-methoxy-3-[7-(4-octylphenyl)-heptyloxy]-1-propanol used as starting material is obtained in the following manner: 4-octylbenzene is reacted with the ethyl ester acid chloride of pimelic acid in the presence of aluminium chloride in nitrobenzene to give 7-(4-octylphenyl)-7-oxoheptanoic acid ethyl ester (m.p. 38°–40° C.). Subsequent hydrogenation in the presence of palladium on charcoal in ethanol with the addition of some perchloric acid gives 7-(4-octylphenyl)-heptanoic acid ethyl ester (oily substance), reduction of which with lithium aluminium hydride gives 7-(4-octylphenyl)-heptanol (oily substance). Reaction with phosphorus tribromide gives the corresponding bromide (oil) which is reacted with the monosodium salt of 2-methoxy-1,3-propandiol.

(d) 2-methoxy-3-(5-dodecyloxypentoxy)-1-propanol (oily substance) as starting material: [2-methoxy-1-(5-dodecylpentoxy)-3-propyl]-(2-trimethylammonium-ethyl) phosphate containing 1 mole of water of crystallization:

in a yield of 31% of theory; m.p. 75° C. (sinters), 234°-236° C. (decomp.)

(e) 2-methoxy-3-(12-pentoxydodecyloxy)-1-propanol (oily substance) as starting material:

[2-methoxy-1-(12-pentoxydodecyloxy)-3-propyl]-(2-trimethylammonium-ethyl) phosphate containing 2 moles of water of crystallization:

in a yield of 27% of theory; m.p. 60° C. (sinters), 220°-223° C.;

(f) 2-methoxy-3-(5-dodecylthiopentoxy)-1-propanol (wax-like substance) as starting material:

[2-methoxy-1-(5-dodecylthiopentoxy)-3-propyl]-(2-trimethylammonium-ethyl) phosphate containing 2 moles of water of crystallization in a yield of 12% of theory; m.p. 60° C. (sinters), 227°-230° C. (decomp.);

(g) 2-methoxymethyl-2-methyl-3-octadecyloxy-1-propanol (wax-like substance) as starting material: (2-methoxymethyl-2-methyl-1-octadecyloxy-3-propyl)-(2-trimethylammonium-ethyl) phosphate containing 4 moles of water of crystallization in a yield of 33% of theory; m.p. 100° C. (sinters), 230°-233° C. (decomp.).

The 2-methoxymethyl-2-methyl-3-octadecyloxy-1-propanol used as starting material is obtained in the following manner: 2-methoxymethyl-2-methylmalonic acid diethyl ester is reduced with lithium aluminium hydride to give 2-methoxy-2-methyl-1,3-propandiol (b.p.$_{12}$: 122°-124° C.) and reacted with octadecyl bromide in the form of its monosodium salt.

(h) 2,2-bis-methoxymethyl-3-hexadecyloxy-1-propanol (wax-like substance) as starting material:

(2,2-bis-methoxymethyl-1-hexadecyloxy-3-propyl)-(2-trimethylammonium-ethyl) phosphate containing 1.5 moles of water of crystallization in a yield of 31% of theory; m.p. 60° C. (sinters), 225°-230° C. (decomp.).

EXAMPLE 2

S-(2-methoxy-1-octadecyloxy-3-propyl)-(2-trimethylammonium-ethyl) phosphate

A solution of 2.76 g. triethylamine and 2.35 g. 2-bromoethylphosphoric acid ester dichloride in 30 ml. toluene is added dropwise at 0° C. to a solution of 2.87 g. 2-methoxy-3-octadecyloxy-1-propanethiol (wax-like substance). The reaction mixture is stirred for 5 hours at 0° C. and overnight at ambient temperature, mixed with 31 ml. 0.1N potassium chloride solution and vigorously stirred for 1 hour at 0° C. and for 2 hours at ambient temperature. The organic phase is separated off, dried and evaporated. There are obtained 2.3 g. of an oily residue which are dissolved in 25 ml. anhydrous methanol/25 ml. anhydrous chloroform. The solution is saturated with dry trimethylamine and heated under reflux for 20 hours. The reaction mixture is then evaporated and the residue is dissolved in anhydrous methanol, mixed with 1.2 g. silver acetate and stirred for 4 hours at ambient temperature, the precipitate obtained being filtered off with suction and washed with anhydrous methanol and the filtrate evaporated. After 12 hours, the dark oil obtained is purified over a silica gel column (elution agent: methylene chloride/methanol/water: 65/25/4 v/v/v). The fractions containing the desired product are combined and evaporated, dried over phosphorus pentoxide and triturated with acetone. There is obtained 0.55 g. (13% of theory) of the desired hygroscopic substance which has a melting point of 65° C. (sinters), 273°-274° C. (decomp.). The compound contains 1 mole of water of crystallization.

The 2-methoxy-3-octadecyloxy-1-propanethiol used as starting material is prepared in the following manner: 2-methoxy-3-octadecyloxy-1-propanol is reacted with benzenesulfochloride in anhydrous pyridine to give 2-methoxy-3-octadecyloxy-1-propanol benzene-sulfonate, (oil). This is then reacted with thiorea in butanol to give the isothiuronium salt which is saponified with potassium hydroxide solution and the thiol liberated with hydrochloric acid.

In an analogous manner, there are obtained by using:

(a) 3-heptadecyloxy-1-propanethiol (wax) as starting material:

S-(1-heptadecyloxy-3-propyl)-(2-trimethylammonium-ethyl) thiophosphate containing 2 moles of water of crystallization in a yield of 11% of theory; m.p. 70° C. (sinters), 254°-257° C. (decomp.);

(b) 3-hexadecyloxy-2-methyl-1-propanethiol (oil) as starting material:

S-(1-hexadecyloxy-2-methyl-3-propyl)-(2-trimethylammonium-ethyl) thiophosphate containing 2 moles of water of crystallisation in a yield of 16% of theory; m.p. 65° C. (sinters), 266°-268° C. (decomp.);

(c) 2-benzyl-3-octadecyloxy-1-propanethiol (oil) as starting material:

S-(2-benzyl-1-octadecyloxy-3-propyl)-(2-trimethylammonium-ethyl) thiophosphate containing 2 moles of water of crystallization in a yield of 15% of theory; m.p. 65° C. (sinters), 225°-230° C. (decomp.);

(d) 3-(3-tetradecyloxypropoxy)-1-propanethiol (oil) as starting material:

S-[1-(3-tetradecyloxypropoxy)-3-propyl]-(2-trimethylammonium-ethyl) thiophosphate containing 2 moles of water of crystallization in a yield of 12% of theory; m.p. 65° C. (sinters), 217°-220° C. (decomp.);

(e) 3-(2-pentadecylthioethoxy)-1-propanethiol (oil) as starting material:

S-[1-(2-pentadecylthioethoxy)-3-propyl]-(2-trimethylammonium-ethyl) thiophosphate containing 2.5 moles of water of crystallization in a yield of 9% of theory; m.p. 58° C. (sinters), 153°-156° C. (decomp.);

(f) 2-(2-methoxyethoxy)-3-octadecyloxy-1-propanethiol (oil) as starting material:

S-[2-(2-methoxyethoxy)-1-octadecyloxy-3-propyl]-(2-trimethylammonium-ethyl) thiophosphate containing 3 moles of water of crystallization in a yield of 18% of theory; m.p. 60° C. (sinters), 219°-221° C. (decomp.).

EXAMPLE 3

[1-(12-Pentyloxydodecyloxy)-3-propyl]-(2-trimethylammonium-ethyl) phosphate

The monosodium salt of 1,12-dodecanediol is reacted with pentyl bromide to give 12-pentoxydodecanol which, after elution on a silica gel column with ligroin-methyl ethyl ketone (4:1 v/v), gives a thin layer chromatographically uniform oil. The yield is 52% of theory. This is then brominated with phosphorus tribromide in the presence of pyridine and, after fractionation on a silica gel column (diethyl ether-ligroin 1:99 v/v as elution agent) gives 47% of theory of thin layer chromatographically uniform oily 12-pentoxydodecyl bromide. This bromide is reacted with the monosodium salt of 1,3-propanediol and then gives, in a yield of 56% of theory, after column purification (elution agent diethyl ether-ligroin 1:1 v/v), 3-(12-pentoxydodecyloxy)- propanol; m.p. 25° C. Phosphorylation, hydrolysis and reaction with trimethylamine take place in the manner described in Example 1 to give a yield of 41% of theory of the desired product; m.p. 63° C. (sinters), 240°–243° C. (decomp.). It crystallizes with 1 mole of water of crystallization.

EXAMPLE 4

[1-(5-Dodecyloxypentyloxy)-3-propyl]-(2-trimethylammonium-ethyl) phosphate

In a manner analogous to that described in Example 3, there are obtained the following intermediates:

5-dodecyloxypentanol; yield 46% of theory; oil; elution agent diethyl ether-ligroin (1:1 v/v);

5-dodecyloxypentyl bromide; yield 64% of theory; oil; elution agent diethyl ether-ligroin 1:99 v/v);

3-(5-dodecyloxypentoxy)-propanol; yield 55% of theory; m.p. 25° C.; elution agent diethyl ether-ligroin (1:1 v/v).

The desired choline ester is prepared in a manner analogous to that described in Example 1. The yield is 47% of theory and the product contains 1 mole of water of crystallization; m.p. 53° C. (sinters), 242°–245° C., (decomp.).

EXAMPLE 5

[1-(2-Pentadecylthioethoxy)-3-propyl]-(2-trimethylammonium-ethyl) phosphate

In a manner analogous to that described in Example 3, there are obtained the following intermediates:

2-pentadecylthioethanol; m.p. 44°–46° C., from the sodium salt of mercaptoethanol and 9-bromopentadecane; yield 97% of theory; elution agent diethyl ether-ligroin (1:1 v/v);

2-pentadecylthioethyl bromide; oil; yield 93% of theory; purification as above;

3-(2-pentadecylthioethoxy)-propanol; m.p. 38°–40° C.; yield 12% of theory; purification as above.

The desired choline ester is obtained in a yield of 24% of theory in a manner analogous to that described in Example 1 in the form of the dihydrate which has a decomposition point of 245° C.

EXAMPLE 6

[1-(2-Pentadecyloxyethoxy)-3-propyl]-(2-trimethylammonium-ethyl) phosphate

In a manner analogous to that described in Example 3, there are obtained the following intermediates:

2-pentadecyloxyethanol; gradually solidfying oil; yield 29% of theory; elution agent ligroin-diethyl ether (1:1 v/v);

2-pentadecyloxyethyl bromide; oil; yield 60% of theory; elution agent diethylether-ligroin (1:99 v/v);

3-(2-pentadecyloxyethoxy)-propanol; m.p. 30° C.; yield 25% of theory; elution agent diethyl ether-ligroin (1:2 v/v).

The desired choline ester is obtained analogously to Example 1. The yield is 21% of theory, after column purification, in the form of a sticky product. It is obtained as a hygroscopic monohydrate.

EXAMPLE 7

(1-Hexadecyloxycarbonyloxy-3-propyl)-(2-trimethylammonium-ethyl) phosphate

Chloroformic acid hexadecyl ester, obtained from cetyl alcohol and phosgene in the presence of dimethylaniline in a yield of 95% of theory in the form of an oil, is reacted with the monosodium salt of 1,3-propanediol and eluted on a silica gel column with ligroindiethyl ether (1:1 v/v). There is thus obtained, in a yield of 22% of theory, hexadecyl-(3-hydroxypropyl)carbonic acid ester (m.p. 28°–32° C.), which is phosphorylated in a manner analogous to that described in Example 1. The desired choline ester is obtained in a yield of 32% of theory. The monohydrate sinters at 55° C. and melts, with foaming, at 178° C.

EXAMPLE 8

(2-Octadecyloxyethyl)-(2-trimethylammonium-ethyl) phosphate

From the monosodium salt of ethyleneglycol and octadecyl bromide, there is obtained, in a yield of 44% of theory, 2-octadecyloxyethanol (m.p. 39°–41° C.). Elution is carried out on a silica gel column with diethyl ether-ligroin (1:3 v/v). The preparation of the choline ester takes place in the manner described in Example 1. The desired compound is obtained in a yield of 35% of theory in the form of the monohydrate; m.p. 59° C. (sinters), 243°–248° C. (decomp.).

EXAMPLE 9

(1-Hexadecyloxy-4-butyl)-(2-trimethylammonium-ethyl) phosphate

From the monosodium salt of 1,4-butanediol, by reaction with hexadecyl bromide, there is obtained, in a yield of 69% of theory, after column purification (diethyl ether-ligroing 1:1 v/v as elution agent), 4-hexadecyloxybutanol (m.p. 36°–40° C.). The choline ester formation is carried out analogously to Example 1. The desired compound is obtained as a dihydrate in a yield of 20% of theory; m.p. 62° C. (sinters), 235°–238° C. (decomp.).

EXAMPLE 10

In a manner analogous to that described in Example 1, there are obtained, by the use of (a) 2-allyl-3-octadecyloxy-1-propanol (oil) as starting material:

(2-allyl-1-octadecyloxy-3-propyl)-(2-trimethylammonium-ethyl) phosphate containing 2 moles of water of crystallization in a yield of 41% of theory; m.p. 70° C (sinters), 235°–240° C. (decomp.);

(b) 3-hexadecyloxy-2-(2-propynyl)-1-propanol (oil) as starting material:

[1-hexadecyloxy-2-(2-propynyl)-3-propyl]-(2-trimethylammonium-ethyl) phosphate containing 1 mole of water of crystallization in a yield of 22% of theory; m.p. 60° C. (sinters), 225°–237° C. (decomp.).

The 3-hexadecyloxy-2-(2-propynyl)-1-propanol used as starting material is obtained by reacting the monosodium salt of 2-(2-propynyl)-1,3-propanediol (oil) with hexadecyl bromide.

(c) 2-benzyloxymethyl-3-heptadecyloxy-1-propanol (wax) as starting material:

(2-benzyloxymethyl-1-heptadecyloxy-3-propyl)-(2-trimethylammonium-ethyl) phosphate containing 2 moles of water of crystallization in a yield of 38% of theory; m.p. 60° C. (sinters), 225°–230° C. (decomp.).

The 2-benzyloxymethyl-3-heptadecyloxy-1-propanol used as starting material is obtained by reacting 2-isopropyl-5-hydroxymethyl-1,3-dioxan with benzyl bromide to give 2-isopropyl-5-benzyloxymethyl-1,3-dioxan (oil), subsequent splitting with sulfuric acid and reaction with an equimolar amount of heptadecyl bromide.

(d) 2-methyl-3-(3-tetradecyloxypropoxy)-1-propanol (oil) as starting material:

[2-methyl-1-(3-tetradecyloxypropoxy)-3-propyl]-(2-trimethylammonium-ethyl) phosphate containing 1 mole of water of crystallization in a yield of 26% of theory; m.p. 80° C. (sinters), 234°-236° C. (decomp.);

(e) 2-benzyl-3-octadecyloxy-1-propanol (m.p. 38°-41° C.) as starting material:

(2-benzyl-1-octadecyloxy-3-propyl)-(2-trimethylammonium-ethyl) phosphate containing 3 moles of water of crystallization in a yield of 20% of theory; m.p. 65° C. (sinters), 232°-235° C. (decomp.);

(f) 3-(10-heptyloxydecyloxy)-2-(2-methoxyethoxy)-1-propanol (oil) as starting material:

[1-(10-heptyloxydecyloxy)-2-(2-methoxyethoxy)-3-propyl]-(2-trimethylammonium-ethyl) phosphate containing 2 moles of water of crystallization in a yield of 20% of theory; m.p. 70° C. (sinters), 220°-223° C. (decomp.);

(g) 4-(2-hexadecylthioethoxy)-2-butanol (paste) as starting material:

[4-(2-hexadecylthioethoxy)-2-butyl]-(2-trimethylammonium-ethyl) phosphate containing 3.5 moles of water of crystallization in a yield of 3% of theory; m.p. 110° C. (sinters), 214°-219° C.;

(h) 3-heptadecyloxy-2-methylthiomethyl-1-propanol (wax) as starting material:

(1-heptadecyloxy-2-methylthiomethyl-3-propyl)-(2-trimethylammonium-ethyl) phosphate containing 3 moles of water of crystallization in a yield of 29% of theory; m.p. 60° C. (sinters), 235°-240° C. (decomp.).

The 3-heptadecyloxy-2-methylthiomethyl-1-propanol used as starting material is prepared in the following manner: 2-isopropyl-4-hydroxymethyl-1,3-dioxan is reacted with benzenesulfochloride to give the corresponding benzenesulfonate (m.p. 63°-65° C.). By reaction thereof with sodium methyl mercaptide, there is obtained 2-isopropyl-4-methylthiomethyl-1,3-dioxan (b.p.$_{0.1}$: 74°-77° C.), from which, by acid treatment, there is prepared 2-methylthiomethyl-1,3-propanediol (oil), reaction of which with an equimolar amount of heptadecyl bromide gives the desired starting material.

EXAMPLE 11

(2-n-Butylthio-1-octadecyloxy-3-propyl)-(2-trimethylammonium-ethyl) phosphate 2 ml. Triethylamine in 15 ml. anhydrous methylene chloride are added at 0° C. to 0.6 g. (4.2 mMole) 2-chloro-2-oxo-1,3,2-dioxaphospholane in 15 ml. anhydrous methylene chloride, as well as 1.1 g. (2.65 mMole) 2-n-butylthio-3-octadecyloxy-1-propanol (wax) in 15 ml. methyl chloride. The reaction mixture is stirred for 1 hour at 0° C. and then overnight at ambient temperature, mixed with 10 ml. water and the organic phase is separated off, dried and evaporated. The residue is dissolved in 30 ml. anhydrous acetonitrile, dry trimethylamine is passed in for 10 minutes and the solution is heated for 12 hours in an autoclave at 70° C. After cooling, the precipitate obtained is filtered off with suction and washed with acetonitrile and the precipitate is dissolved in methanol and evaporated. The residue is purified over 100 g. silica gel (elution agent: methylene chloride/methanol/water 65/25/4 v/v/v). The fractions containing the desired product are combined and evaporated, dried over phosphorus pentoxide and triturated with acetone. There is obtained 0.33 g. (about 21% of theory) of the desired product; m.p. 60° C. (sinters), 217°-220° C. The compound contains 1 mole of water of crystallization.

The 2-n-butylthio-3-octadecyloxy-1-propanol used as starting material is obtained in the following manner: 2-benzyloxy-3-octadecyloxy-1-propanol is reacted with dihydropyran to give the corresponding tetrahydropyranyl derivative (oil), the benzyl protective group is removed by hydrogenation in the presence of palladium/charcoal catalyst and the reaction product obtained is reacted with benzenesulfochloride to give 2-benzenesulfonyloxy-3-octadecyloxy-1-tetrahydropyranyloxypropane (wax). Reaction thereof with the sodium salt of n-butylmercaptan gives 2-n-butylthio-3-octadecyloxy-1-tetrahydropyranyloxypropane (oil), from which the tetrahydropyranyl protective group is split off under acidic conditions.

In analogous manner, by the use of 2-hexadecylthio-3-methoxy-1-propanol (wax) as starting material, there is obtained (2-hexadecylthio-1-methoxy-3-propyl)-(2-trimethylammonium-ethyl) phosphate containing 2.5 moles of water of crystallization, in a yield of 22% of theory; m.p. 179° C. (sinters), 195°-215° C.

EXAMPLE 12

[2-Hydroxy-1-(3-tetradecyloxypropoxy)-3-propyl]-(2-trimethylammonium-ethyl) phosphate 0.9 g. 2-Benzyloxy-3-(3-tetradecyloxypropoxy)-1-propanol phosphoric acid monocholine ester (m.p. 65° C. (sinters), 238°-240° C.) are hydrogenated at ambient temperature in 200 ml. ethanol in the presence of 0.9 g. palladium/charcoal as catalyst. After the take up of hydrogen has ceased, the reaction mixture is filtered with suction and the filtrate is evaporated, dried over phosphorus pentoxide and the residue is triturated with acetone. There are obtained 0.45 g. (about 60% of theory) of the desired compound; m.p. 70° C. (sinters), 260°-262° C. (decomp.). The compound contains 1 mole of water of crystallization.

The 2-benzyloxy-3-(3-tetradecyloxypropoxy)-1-propanol phosphoric acid monocholine ester used as starting material is prepared in the following manner: a solution of 3.5 g. 2-benzyloxy-3-(3-tetradecyloxypropoxy)-1-propanol (oil) in 40 ml. anhydrous tetrahydrofuran is added dropwise at 0° C. to 1 ml. phosphorus oxychloride in 8 ml. anhydrous tetrahydrofuran. The reaction mixture is stirred for 1 hour at 0° C. and for 1 hour at ambient temperature, then cooled, mixed with 16 ml. 1N aqueous sodium hydroxide solution and further stirred for 2 hours at ambient temperature. 40 ml. alcoholic hydrochloric acid, 80 ml. chloroform and 40 ml. water are added thereto and the organic phase is separated off and evaporated. The residue is heated under reflux for 4 hours in 80 ml. 80% aqueous dioxan, evaporated and the residue is taken up in 40 ml. chloroform and the solution shaken with 20 ml. 2N hydrochloric acid. The organic phase is separated off, dried and evaporated. There are obtained 3.4 g. (about 77% of theory) phosphoric acid mono-[2-benzyloxy-3-(3-tetradecyloxypropoxy-1-propyl]ester as a wax-like substance.

3.4 g. of this compound are dissolved in 100 ml. anhydrous pyridine and 0.8 g. 2-bromoethanol and 4.5 g. 2,4,6-triisopropylbenzensulfochloride are added thereto. The reaction mixture is stirred overnight at ambient temperature, cooled, mixed with 40 ml. 0.1N aqueous potassium chloride solution, stirred for 2 hours, acidified with concentrated hydrochloric acid, shaken out with methylene chloride and the organic phase is dried and evaporated. There are obtained 3.9 g. (about 95% of theory) phosphoric acid (2-bromoethyl)-[2-benzyloxy-3-(3-tetradecyloxypropoxy)-1-propyl]ester in the form of an oiy substance.

3.9 g. of this ester are dissolved in a mixture of 50 ml. methanol and 50 ml. chloroform. Dry trimethylamine is passed in for 10 minutes and the reaction mixture is heated under reflux for 20 hours, evaporated and the residue is taken up in 75 ml. methanol, mixed with 1.5 g. silver acetate, stirred for 2 hours, filtered with suction and the filtrate evaporated. The residue is purified over 100 g. silica gel (elution agent: methylene chloride/methanol/water 65/25/4 v/v/v). There is obtained 1.4 g. (about 35% of theory) of the desired substance; m.p. 65° C. (sinters), 238°–240° C. The compound contains 2 moles of water of crystallization.

In an analogous manner, by the use of 2-benzyloxymethyl-3-heptadecyloxy-1-propanol phosphoric acid monocholine ester (m.p. 60° C. (sinters), 225°–230° C. (decomp.)) (see Example 10c) as starting material, there is obtained (1-heptadecyloxy-2-hydroxy-3-propyl)-(2-trimethylammonium-ethyl) phosphate containing 4 moles of water of crystallization, in a yield of 57% of theory; m.p. 60° C. (sinters), 228°–230° C. (decomp.).

EXAMPLE 13

[4-(2-(2-Hexadecanesulphinylethoxy)-2-butyl]-(2-trimethylammonium-ethyl) phosphate 1 g. of the compound described in Example 10(g) is dissolved in 10 ml. glacial acetic acid and 0.2 ml. 30% hydrogen peroxide added dropwise thereto at 0° C. During subsequent stirring of the reaction mixture at ambient temperature, the progress of the oxidation is monitored by thin layer chromatography. After standing overnight, the reaction mixture is evaporated. The residue is applied to a silica gel column and eluted with the mixture used in Example 1. There is thus obtained 0.65 g. (58% of theory) of the desired compound in the form of white crystals which contain 2.5 moles of water of crystallization; m.p. 49° C. (sinters), 209°–218° C.

(a) In an analogous manner, by reaction with an excess of hydrogen peroxide, there is obtained [4-(2-hexadecanesulfonylethoxy)-2-butyl]-(2-trimethylammonium-ethyl) phosphate; m.p. 49° C. (sinters), 199°–209° C. (decomp.). The yield is 39% of theory. The product is obtained in the form of white crystals containing 2.5 moles of water of crystallization;

(b) In an analogous manner, by oxidation of the compound described in Example 10(h), there is obtained (1-heptadecyloxy-2-methanesulfonylmethyl-3-propyl)-(2-trimethylammonium-ethyl) phosphate containing 2 moles of water of crystallization; m.p. 55° C. (sinters), 215°–220° C. (decomp.). The yield is 63% of theory.

The compounds of the invention possess outstanding therapeutic properties and the compounds can be administered as set forth at pages 12 et seq supra.

The compounds were tested for their cytotoxic effect on tumor cells of the mouse in the following tests.

(a) Cytotoxic Effectiveness

The target cells were, in one series of tests, cells of a methylcholanthrene induced tumor (MethA) which was passaged in the mouse as ascites and, in a second series of tests, Abelson-8.1-lymphoma cells (Abls) which were cultured in vitro.

For these tests $5 \times 10^4$/ml of the cells were cultivated with the below-indicated new sulfur-containing phospholipid test compounds, at various concentrations, for 24 hours, in Dulbecco's Modified Eagle's Medium enriched with 10% heat-inactivated fetal calves serum, $5 \times 10^{-5} m$ mercaptoethanol, 50 U penicillin and 50 μg streptomycin/ml. The cultivation was performed at 95% atmospheric humidity, at 37° C., and at 10% $CO_2$ content in a humidified incubating thermostatic chamber.

The effectiveness of the test compounds was measured by comparing the growth of the tumor cells in the medium with and without the sulfur-containing phospholipid compounds, i.e., a control test was run using a control culture without test compound. In addition each series of experiments included a comparison tests using, instead of the test compounds of the invention, 1-octadecyl-2-methyl glycero-3-phosphorylcholine (as disclosed in German Patent publication No. 26 19 686), referred to below as Compound A. The growth of the MethA cells was measured by introduction of $^3$H-thymidine into the DNA of the cells; the growth of the Abls cells was measured by determining the alkaline phosphatase activity of an aliquot of the cultures. For each test substance there was determined that concentration at which thymidine introduction of alkaline phosphatase activity, respectively, was reduced by 50% relative to the untreated tumor cell control.

In the Table below the effectiveness of the substances of the invention in the above tests is set forth. The superiority of the inventive compounds, relative to the test compound set forth above, is expressed by a factor which is the ratio of the concentration of the comparison compound required for the 50% reduction effectiveness divided by the concentration required of the test compound for the same 50% reduction effect.

(b) Thrombocyte Aggregation

In a further series of tests, the thrombocyte aggregation effect of the novel compounds of the invention was measured. There was determined the platelet aggregation action of the new sulfur-containing phospholipid compounds, by centrifuging blood from healthy human donors for 10 minutes at 100 g in order to obtain the platelet-rich plasma. The plasma was heated to 37° C. in an aggregometer, and then the test compounds were added. The amounts listed in the Table below represent the concentration of the substances which starts an irreversible platelet aggregation.

TABLE

| | Tumor cell cytotoxicity factor* | Platelet aggregation mg/ml |
|---|---|---|
| Compound A (2-ethyl-1-octadecyloxy-3-propyl)-(2-trimethylammonium-ethyl) phosphate | 1.0 | <0.05 |
| (2-methoxymethyl-2-methyl-1-octadecyloxy-3-propyl)-(2-trimethylammonium-ethyl) phosphate | 1.0 | >2 |
| (2,2-bis-methoxymethyl-1-hexadecyloxy-3-propyl)-(2-trimethylammonium-ethyl) phosphate | 0.8 | >2 |
| 5-(2-methoxy-1-octadecyloxy-3-propyl)-(2-trimethylammonium-ethyl) phosphate | 0.9 | >1 |
| [1-(2-Pentadecyloxyethyoxy)-3-propyl]-(2-trimethylammonium-ethyl) phosphate | 1.0 | >1 |
| (2-Octadecyloxyethyl)-(2-trimethyl- | 0.60 | >1 |

TABLE-continued

| | Tumor cell cytotoxicity factor* | Platelet aggregation mg/ml |
|---|---|---|
| ammonium-ethyl) phosphate | 0.7 | >1 |

*Factor = $\dfrac{C_{50} \text{ compound A}}{C_{50} \text{ compound X}}$

It will be understood that the specification and examples are illustrative but not limitative of the present invention and that other embodiments within the spirit and scope of the invention will suggest themselves to those skilled in the art.

What is claimed is:

1. Phospholipid compound, designated (2-ethyl-1-octadecyloxy-3-propyl)-(2-trimethylammonium-ethyl) phosphate.
2. Phospholipid compound, designated (2-methoxymethyl-2-methyl-1-octadecyloxy-3-propyl)-(2-trimethylammonium-ethyl) phosphate.
3. Phospholipid compound, designated (2,2-bis-methoxymethyl-1-hexadecyloxy-3-propyl)-(2-trimethylammonium-ethyl) phosphate.
4. Phospholipid compound designated (2-allyl-1-octadecyloxy-3-propyl)-(2-trimethylammonium-ethyl) phosphate.
5. Phospholipid compound designated [1-hexadecyloxy-2-(2-propynyl)-3-propyl]-(2-trimethylammonium-ethyl) phosphate.
6. Phospholipid compound designated (2-hexadecylthio-1-methoxy-3-propyl)-(2-trimethylammonium-ethyl) phosphate.

* * * * *